United States Patent [19]

Haisma

[11] Patent Number: 4,775,638
[45] Date of Patent: Oct. 4, 1988

[54] SINGLE VIAL TECHNIQUE FOR RADIOLABELING PROTEIN

[75] Inventor: Hidde J. Haisma, Utrecht, Netherlands

[73] Assignee: Centocor, Inc., Malvern, Pa.

[21] Appl. No.: 732,228

[22] Filed: May 8, 1985

[51] Int. Cl.$^4$ ............... G01N 33/534; G01N 33/537; A61K 49/02

[52] U.S. Cl. ................... 436/547; 424/1.1; 424/85.8; 436/548; 436/804; 436/808; 530/389; 530/402; 935/107

[58] Field of Search ............. 436/504, 545, 548, 804, 436/808, 542; 935/106, 110, 107; 424/1.1, 85; 530/389, 402

[56] References Cited

U.S. PATENT DOCUMENTS

| | | | |
|---|---|---|---|
| 4,298,590 | 11/1981 | Bogoch | 436/503 |
| 4,318,902 | 3/1982 | Stephan | 424/85 |
| 4,348,376 | 9/1982 | Goldenberg | 935/108 |

OTHER PUBLICATIONS

N. R. Moudgal et al., "Pituitary Gonadotropins", in B. M. Jaffe et al., (Eds.), *Methods of Hormone Radioimmunoassay*, 2nd Ed., Academic Press, New York, 1979, pp. 173–198.

B. A. Roos et al., "Parathyroid Hormone", in B. M. Jaffe et al., (Eds.), *IBID*, pp. 401–418.

J. L. Vaitukaitis, "Specific Human Chorionic Gonadotropin Assay", in B. M. Jaffe et al., (Eds.), *IBID*, pp. 817–829.

*Nature Directory of Biologicals: 1983 Buyers Guide*, pp. 215 and 218.

Ferens, J. M. et al., *J. Nucl. Med.*, 25:367:370, (1984).

Fraker, P. J. and Speck J. C., *Biochem. Biophys. Res. Commun.* 80:, 849–857, (1970).

Hudson, L. and Hay F. C., *Practical Immunology*, Blackwell Scientific Publications, pp. 239–244.

*Method in Immunology and Immunochemistry*, Williams, C. A. and Chase, M. W., Eds., Academic Press, New York, 1967, pp. 387–391.

Richardson, A. P., et al., *Nucl. Med. Comm.* 7:355–362, 1986.

*Primary Examiner*—Robert J. Warden
*Assistant Examiner*—David A. Saunders
*Attorney, Agent, or Firm*—Hamilton, Brook, Smith & Reynolds

[57] ABSTRACT

A method for radiolabeling protein such as antibody which is performed in a single reaction vessel is described. A sealed reaction vessel having a port for addition and withdrawal of reagents preferably by syringe is used. Reagents for coupling radioisotope to the protein are added to the vessel. For radioiodination procedures, vessels can be pre-coated with the iodine coupling agent iodgen. The protein and the radioisotope are then added to the vessel and the radiolabel reaction allowed to proceed. After the reaction is complete, a resin is added to the vessel to adsorb the uncoupled radioisotope. The entire reaction mixture is then withdrawn from the vessel and the resin is separated from the protein preferably by sterile filtration.

20 Claims, 1 Drawing Sheet

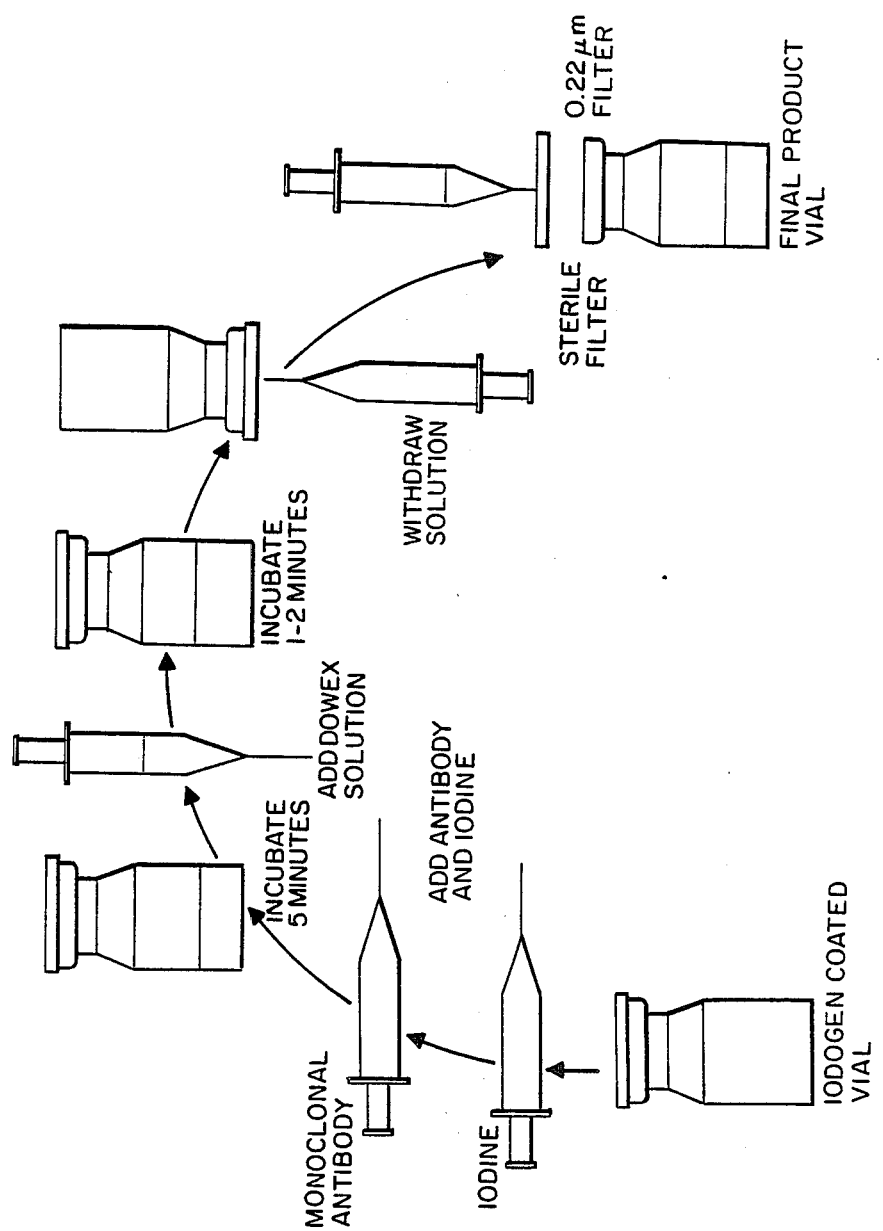

SINGLE VIAL TECHNIQUE FOR RADIOLABELING PROTEIN

DESCRIPTION

FIELD OF THE INVENTION

This invention is in the fields of immunotherapy and immunodiagnostics.

BACKGROUND OF THE INVENTION

Radiolabeled polyclonal and monoclonal antibodies have been used as reagents for diagnostic tumor imaging and as therapeutic agents. As monoclonal antibodies exhibiting better specificity for tumors become available, they are being evaluated for clinical usefulness in diagnosis and radiotherapy of cancer. These procedures require radiolabeled antibodies. Apart from Technetium 99m labeling, techniques for radiolabeling antibody and other protein are often complicated and dangerous and therefore not regularly used in nuclear medicine practice.

Recently, bifunctional chelates have been used to label antibodies with $^{111}$In or $^{67}$Ga for radio-immunoscintigraphy. In most instances, however, $^{123}$I and $^{131}$I remain the radioisotopes of choice for this application. For persons performing the procedure, radioiodination of protein presents several safety hazards. These include direct radiation exposure and potential thyroid accumulation of radioiodine.

Another problem associated with radioiodination procedures is that radioiodinated antibodies lose immunochemical reactivity due to chemical or radiation damage. Radiation damage is worse for antibody labeled to high specific activity. Thus, to retain immunological reactivity of an antibody, the iodination procedure should be mild to minimize damage of the antibody by chemical reagents and it must be performed shortly before using the antibody to minimize damage of the antibody by radioactive decay.

To achieve widespread use of radiolabeled antibody for clinical applications convenient, rapid and safe radiolabeling procedures are needed.

DISCLOSURE OF THE INVENTION

This invention constitutes a method of radio-labeling protein in a single reaction vessel. The radiolabeling reaction (i.e., the coupling of the radioisotope to protein) and the separation of uncoupled radioisotope (that which is not incorporated as label into the protein) are achieved in the same vessel. The method is simple, efficient, and reproducible and it minimizes the safety hazards to persons performing the radiolabeling.

The method of this invention is particularly suited for labeling antibodies (polyclonal and monoclonal) for diagnosis and therapy. Antibody can be labeled by this method to a high specific activity with minimal loss of immune reactivity. However, the procedure can be applied to the radiolabeling of virtually any protein. Although the method is primarily designed for radioiodination, because iodine is the most frequently used radioisotope in radiodiagnostics and radiotherapeutics, it can be adapted for labeling protein with $^{67}$Gallium and $^{111}$Indium radioisotopes.

A sealable reaction vessel is used which has means for the introduction and withdrawal of reagent preferably under sterile or semi-sterile conditions. A vessel which contains a port for syringe injection is preferred. All reagents can be injected and withdrawn from the reaction vial by syringe, thereby reducing the risk of exposure to volatile, toxic reagents.

An oxidizing reagent for coupling the radio-isotope to protein is added to the vial. For iodination of protein the preferred oxidizing reagent is iodogen. Iodogen is a mild oxidizing agent and consequently causes minor damage to the protein being iodinated. Further, iodogen can be coated onto the inner surface of the glass reaction vials, thus permitting the vials to be precoated with the reagent and presealed and supplied for use in that form.

The protein to be labeled and the radioisotope are added to the vial containing the coupling agent. In $^{111}$In and $^{67}$Ga labeling protein should be chelated with a chelating agent for the radioisotope. The protein is added in a buffered solution. For radioiodination of monoclonal antibody by the iodogen labeling technique, the preferred buffer is a borate buffer (about 0.1M at pH 8.0–8.5). The radioisotope can be added to the vial before or after addition of the protein, or it can be added together with the protein. Radioiodine (I$^{123}$, I$^{125}$, or I$^{131}$) is supplied as sodium iodide in NaOH and can be added to the solution of protein in NaOH. $^{67}$Ga is supplied Gallium sulfate and $^{111}$In is provided as Indium chloride.

The radiolabeling reaction is then allowed to proceed. Depending on the type of radiolabeling reaction, the duration and conditions of incubation will vary. Iodination by iodogen catalysis yields about 90% incorporation of iodine into protein after about 5 minutes incubation at room temperature.

After competion of the labeling reaction, an anion exchange resin is added directly to the reaction mixture to adsorb free radioisotope in the mixture. The resin should have a high binding affinity for the radioisotope. A preferred resin for adsorbing free iodine is AG 1X-8 anion exchange resin (Biorad Labs). The AG 1X-8 resin has an extremely high affinity for iodine and adsorbs unincorporated iodine in the reaction mixture almost instantly.

A carrier protein can be added along with the resin to reduce radiation damage to labeled protein. For example, in radioiodination procedures, a carrier protein such as bovine serum albumin can be added with the AG 1X-8 resin. The carrier protein is not radioiodinated to ayy significant degree because adsorption of free iodine by AG 1X-8 resin is rapid and virtually complete, and therefore halts any further radioiodination.

The reaction mixture and resin are withdrawn from the reaction vessel and the labeled protein is separated from the resin. Preferably, separation is accomplished by filtration, employing a filter which has a pore size smaller than the resin particle size. Sterile filtration is the preferred separating technique. In this way the resin containing the unincorporated radioisotope is removed from the radiolabeled antibody preparation and the preparation is sterilized at the same time. Filters having pore sizes (e.g., 0.22 microns) suitable for excluding bacteria are small enough to exclude resins such as AG 1X-8. The sterile-filtered, radiolabeled antibody preparation can be stored until use or injected directly into patients.

BRIEF DESCRIPTION OF THE DRAWINGS

FIG. 1 is a scheme outlining the preferred mode of the method of this invention.

BEST MODE OF CARRYING OUT THE INVENTION

The radiolabeling procedure is performed in a single, sealed reaction vessel. The sealed vessel prevents exodus of hazardous radioisotopes during the procedure. The reaction vessel can be glass or plastic. The vessel has means for the introduction and withdrawal of reactants under sterile or semisterile conditions. Preferably the reaction vessel is a glass vial sealable by a cap (such as a rubber cap) at least a part of which can be pierced by a needle so that all transfers of reagents to and from the vial can be done by syringe. The use of a syringe expedites reagent transfer and offers additional protection against exposure to radioactive material.

Initially, a reagent is added for catalyzing the coupling of the radioisotope to the protein to be labeled. For radioiodination, any of the several conventional radioiodination techniques can be employed. These techniques are discussed in detail in *Immunochemistry in Practice*, A. Johnstone and R. Thorpe, Blackwell Scientific Publications Oxford (1982). The techniques are based on the use of different coupling reagents which catalyze the incorporation of iodine into protein. The coupling agents include iodogen (1,3,4,6-tetrachloro-3,6-diphenylglycuril), chloramine T, lactoperoxidase and iodine monochloride.

The preferred technique of radioiodination is the iodogen technique. Iodogen catalyzed labeling of protein is a mild procedure which causes little damage to protein. Further, the iodogen can be coated on the inner surface of the reaction vial. Thus, iodogen-coated reaction vials can be prepared in advance for use in the method. The vials can be coated simply by adding iodogen to the vial in an organic solvent, such as chloroform, and then evaporating the solvent (generally under a stream of nitrogen). For example, a 20 ml glass vials can be coated with 100 ug iodogen (50 mg/ml iodogen per 2 ml chloroform) and used to iodinate from up to 1 mg of protein. Iodogen coated vials can be sealed and stored until use. Pre-coated vials can be stored ($-20°$ C.) for at least three months with no appreciable loss of activity.

After addition of the oxidizing agent, the vial should be sealed under reduced pressure so that addition of reagents during the method does not produce a positive pressure in the vial which may cause leakage of radioisotope during the labeling procedure. Vials coated in advance can be sealed under vacuum and provided for use.

The radiolabeling reaction is initiated by adding the protein to be radiolabeled and the radioisotope to the vial, preferably by injection with a syringe. Protein is added in a buffered solution. For monoclonal antibody, the preferred buffer is a borate buffer (0.1M borate buffer at pH 8.0–8.5, preferably pH 8.3). Other types of buffers such as phosphate or Tris buffers are suitable. For different types of protein and possibly for some antibodies, the optimal parameters of the buffer solution may vary but can be determined by experimentation.

The radioisotope can be added to the vial either before or after the protein. Alternately, the radioisotope may be premixed with the protein and added to the vial as a single solution.

The iodine radioisotope can be $I^{123}$, $I^{125}$, or $I^{131}$. These radioisotopes are commercially available generally as NaI. The radioiodine can be added in solution of NaOH.

The reaction mixture of protein and radioisotope is then incubated under conditions which permit labeling of the protein. Depending on the radiolabeling technique and the radioisotope, the optimum conditions for the reaction may vary. For iodogen-catalyzed iodination of antibody an incubation period of about 5 minutes at room temperature yields maximum incorporation of iodine into protein (aproximately 90% iodine incorporation). The incubation period can range from 2–30 minutes.

An ion exchange resin is then added to the reaction mixture to bind free radioisotope. The resin can be injected directly into the vial in a solution of a buffer. By adding the ion exchange resin to the reaction mixture, the separation of free radioisotope from bound radioisotope takes place in the vial and the use of an ion exchange or gel filtration column is avoided.

Generally, the type and the amount of resin needed to bind maximal amount of free radioisotope can be ascertained experimentally. For adsorption of free iodine, an anion exchange resin such as Biorad AG 1-X8 (quarternary ammonium groups attached to a styrene divinyl benzene copolymer lattice). This resin, in appropriate concentration, takes up the free iodine in the reaction mixture instantly. The adsorptive capability of AG 1-X8 is dependent on the concentration in the reaction mixture. Other types of resins can be used as long as they are capable of binding free radioisotope, preferably with high affinity.

A carrier protein such as albumin can be added with the ion-exchange resin. The carrier protein reduces radiation damage to the labeled protein and can reduce adsorption of labeled protein to the resin. In radioiodination procedures, when added in conjunction with AG 1-X8 resin, the carrier protein is not iodinated to any significant degree because the affinity of AG 1-X8 resin for iodine is so high and the uptake of iodine so rapid, that the radioiodination reaction is immediately quenched.

The reaction mixture and the suspended resin is then withdrawn from the vessel and the resin and the labeled protein are separated. The preferred way to separate the resin from the labeled protein is by sterile filtration. Filters suitable for sterile filtration range in size from about 0.22 microns to 0.45 microns. These filters will restrict passage of the AG 1-X8 resin and most other anion exchange resins.

A convenient way to filter the reaction mixture is to attach a filter to the tip of the syringe containing the withdrawn reaction mixture and resin. The contents of the syringe are simply pressed through the filter. After passage through the filter, the filtrate containing the labeled antibody is free of resin and sterile. The preparation can be injected directly into a patient or stored until use.

FIG. 1 is a scheme which depicts the preferred mode of the method of this invention.

A glass vial (approximately 20 ml volume) sealed under reduced pressure with a rubber cap and precoated with iodogen (100 mg) is provided.

Na $^{125}$I or Na $^{131}$I (1–10 mCi) in sodium hydroxide is injected into the vial by syringe. Next, a solution of the monoclonal antibody (50 ug - 1 mg/1 ml) in 0.1 M borate buffer pH 8.3 is injected. The vial is incubated at room temperature for about 5 minutes after which a suspension of AG 1-X8 anion exchange resin (2ml; 90% (v/v) resin in phosphate buffered saline) is injected.

After a 1-2 minute incubation period with the resin, the contents of the vial are withdrawn by syringe. The contents are then passed through a sterile filter to remove the resin and any contaminating microorganisms from the preparation.

Employing the preferred mode, the monoclonal antibody OC125 (reactive with 80% of ovarian cancers) was radioiodinated.

Incorporation of iodine into the OC125 antibody was approximately 90%. The antibody could be labeled to specific activities from 5-25 mCi/mg while retaining an immune reactivity of 65-85%. AG 1-X8 resin at a concentration of approximately 50% in the reaction mixture removes 98-100% of non-bound iodine from the labeled antibody preparation.

Three other monoclonal antibodies were radioiodinated by the method. In each case, incorporation of iodine exceeded 90% and immunoreactivity was 70%.

The radioiodination method as exemplified in FIG. 1 and described above stands out for its easiness, as compared to other labeling techniques which require setup of machines. See e.g. James, S. F. W. et al. *Med. Lab. Sci* 40, 67-68 (1983); Ferens, J. M. et al. *J. Nucl. Med.* 25, 367-370 (1984). All transfers from and to the iodination vial are made with syringes so that exposure to volatile iodine is minimized. The entire procedure can be performed in less than 15 minutes. Reaction volumes can be small. For example, a milligram of antibody can be labeled to a specific activity of 5-25 mCi/mg in 1 ml reaction volume. The final antibody preparation is sterile and pyrogen-free and ready for use in clinical applications.

The iodogen labeling method secures minimal damage of protein during the iodination. The reaction is slow as compared with chloramine T iodination but this makes the reaction more controllable. The reaction takes approximately 5 minutes. With minor modification chloramine T, lactoperoxidase, or iodine monochloride iodination can be performed in the same way.

The method of this invention will greatly facilitate the use of iodinated antibodies for imaging or therapy because it is safe and simple, the method can be performed in any radionuclide laboratory thus making radioimmunodetection and antibody guided radiation therapy less restricted to specialized centers.

For convenience, the materials and reagents required to perform the radiolabeling procedure can be assembled in a kit. For example, the materials and reagents for performance of the radioiodination can include:
  (a) a sealed, iodogen-coated reaction vial;
  (b) a solution of radioiodine, e.g., a reductant free solution of Na $^{125}$I in NaOH solution; and
  (c) iodine binding resin either dry or suspended in solution, e.g., AG 1-X8 resin in PBS.

The resin can be supplied in a buffer solution containing a carrier protein such as bovine serum albumin. Additional components of the kit can include a buffer solution for the protein to be radioiodinated, sterile filters (generally 0.22 microns in pore size) for separating the resin from the protein and concomitantly sterilizing the preparation, a syringe, etc.

The invention is further illustrated by the following exemplification.

EXEMPLIFICATION

MATERIALS

Iodine-131 was obtained at high specific activity as a reductant free solution in NaOH pH 7-11, containing 5 mg I per 100 mCi I-131 at 200 mCi/ml (Amersham). Iodine-125 was obtained in a comparable solution at 500 mCi/mL (Cintichem).

Five monoclonal antibodies were used in these studies: OC125, 1116NS 19-9, 115D8, R11D10 and A5C3. Antibody OC125 (IgG$_1$) is directed against the antigenic determinant CA125 found on a majority of epithelial ovarian tumors and has been used to develop an immunoradiometric assay. Similarly, antibody 1116NS 19-9 (IgG$_1$), originally prepared against a colorectal carcinoma cell line, has been used to develop an immunoradiometric assay and for tumor visualization by radioimmunoscintigraphic techniques. Antibody 115D8 was prepared against human milk fat globules and binds to the majority of breast carcinomas. Antibody A5C3 is directed against hepatitis B surface antigen and antibody R11D10 against human cardiac myosin. All chemicals were of reagent grade quality and were prepared as sterile, pyrogen-free solutions.

METHODS

Radioiodination

Antibody was iodinated using a modification of the iodogen (1, 3, 4, 6 tetrachloro-3,6-diphenylglycoluril) method Fraker, P. J. and Speck, J. C. Biochem. Biophys Res. Commun. 80 849-857 (1978). Labeling was done in 1 ml 0.1M borate buffer at room temperature for 10 minutes in a 20 ml glass vial previously coated with 2 ml 50 mg/ml iodogen. Fifty micrograms to 1 mg of antibody was reacted with one to ten millicuries of I-125 or I-131. The reaction was quenched with 2 ml ion exchange resin (AG1-X8, 100-200 mesh; Biorad Labs.) solution (v/v 90% resin in PBS). After 1 minute the solution was withdrawn from the vial and sterile filtered into another vial (FIG. 1).

Resin capacity/concentration/time

To determine capacity of the resin, 1 ml 50% (v/v) resin was incubated with increasing amounts of NaI containing I-125. After 5 minutes incubation, bound and free I-125 were determined. These values were used to compute the maximum amount of Iodine which could be adsorbed by different concentrations of resin (v/v). I-125 was added and incubated for 5 minutes. Bound and free I-125 were determined and minimal concentration of resin was calculated. To 1 ml resin 50% (v/v) I-125 was added and incubated for 30 seconds to 5 minutes. Bound and free I-125 were determined and minimal time for reaction computed.

Assay of Percent Incorporated Iodine and Free Iodine in Final Product

Prior to the addition of ion exchange resin, a sample was withdrawn from the iodination vial and assayed for free and bound iodine using gel filtration HPLC (TSK 63,000 SW). HPLC equipment (Waters Associates) was fitted with a UV monitor (214 nm) and a radiation detector (Vector Model). The final product, which has been mixed with ion exchange resin and filtered, was assayed in identical fashion. Percent iodine incorporation was arrived at by calculating the surface area under the peak of the radiation profile of antibody and free iodine.

Assay of Immune Reactive Fraction

This assay was performed as described by Lindmo, T. et al. *J. Immunol. Meth.* 72 77-89 (1984). For OC125 antibody, to one concentration of radiolabeled antibody, serial dilutions of OVCA 433 (Berkowitz, R. S. et al. Am. J. Obstet. Gynecol. 146 607-612 (1983) cells were added and incubated for 4 hrs at 4° C. The cells were washed and cell bound radioactivity was determined. To calculate the immune reactive fraction, the ratio of total applied radiolabeled antibody to specifically bound radioactivity was plotted against the inverse of cell concentration. Estimates of immunoreactivity of 1116NS 19-9 R111D10 was performed by the percentage binding of a sample of the radiolabeled antibodies to an affinity chromatography column of 1116NS 19-9 antigen or myosin.

Quality Control

Product sterility and a pyrogenicity was tested by incubating with thioglycolate medium. Pyrogenicity was tested using the Limulus Amebocyte Lysate (LAL) method.

RESULTS

Radiolabelling of Monoclonal Antibodies

FIG. 1 illustrates schematically the system developed for radioiodination of monoclonal antibodies. The system utilizes a sealed iodogen coated reaction vial, a buffered monoclonal antibody solution, ion exchange resin solution and 0.22 mM filter to obtain a final sterile, pyrogen-free product ready for injection in less than 10 minutes.

Using OC125 as the target antibody, we found that 0.1 M borate buffer pH8.3 was favorable over phosphate or Tris buffers. Incorporation of iodine into OC125 usually appeared to reach its maximum by 5 minutes of incubation, however, incubation was done for 10 minutes to show complete reaction. In order to remove free iodine, AG 1-X8, a very strong anion exchange resin with a high affinity for iodine, was chosen. In order to investigate the amount resin needed to remove free iodine, an iodine solution with different amounts of resin was used. The percent iodine removed was dependent on the concentration of resin but not on the amount of resin in the reaction mixture. One ml of 50% resin could bind up to 0.01M of NaI. There was no increase in the percentage iodine removed after 0.5 minutes of incubation.

Free iodine was not detected in the final product in the majority of molecules. Occasionally, 1-2% free iodine could be detected. The removal of the resin from the reaction mixture was achieved by filtering through a 0.22 micron Millex ™ filter which at the same time sterilized the product. The final yield was 80-90% of initial iodine, and 80-90% of antibody. For 8 replicates using $^{125}I$ and 4 replicates using $^{131}I$ to label the antibody OC125, it was found that incorporation was 90±4% in each case (Table 1) using the final system.

TABLE I

| Radio-nuclide | Replicates | Fraction of Iodine Incorporated (%) | Immune Reactivity of Final Product (%) |
|---|---|---|---|
| $^{125}I$ | 8 | 90 ± 4 | 82 ± 8 |
| $^{131}I$ | 4 | 90 ± 4 | 66 ± 5 |

The immune reactivity of this iodinated OC125 determined using the cell binding assay described in the Methods section. Plots of A/Sp versus 1/[C] for $^{125}I$-OC235 and $^{131}I$-OC125 were made. Results of iodinations are summarized in Table I. Unexpectedly, the immune reactivity of iodinated OC125 was 82+8% (range 73-96) for I-125 and 65±5% (range 59-71) for I-131. The immune reactivity slightly decreased with higher specific activities, being ±83% for 1-5 mCi/mg I-125 and ±73% for 25-30 mCi/mg I-125. For I-131 immune reactivity dropped from ±71% for 1-5 mCi/mg to ±63% for 25-30 mCi/mg.

The terminal sterilization of iodinated OC125 by millipore filtration assured a sterile product and sterility tests were routinely negative. The LAL test never exceed one endotoxin units per ml. Similar results (Table II) were found using three other monoclonal antibodies as targets for radioiodination. In each case incorporation of iodine exceeded 90 percent. Immunoreactivities all exceeded 70 percent. Both IgG$_1$ and IgG$_2$ antibodies could be iodinated successfully using the system. All reagents could be prepared in sterile, pyrogenfree fashion.

TABLE II

| Antibody | Radio-Nuclide | Replicates | Fraction of Iodine Incorporated (%) | Immuno-Reactivity Final Prod. (%) |
|---|---|---|---|---|
| 1116NS 19-9 (IgG$_{2a}$) | $^{125}I$ | 4 | 90 ± 4 | 72 ± 4 |
| R11D10 (IgG$_{2a}$) | $^{125}I$ | 2 | 89 ± 1 | 86 ± 2 |
| 115D8 (IgG$_{2b}$) | $^{125}I$ | 2 | 88 | 77 |

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of labeling an antibody with a radioisotope, comprising the steps of:
    (a) providing a sealed vessel containing a reagent which catalyst the coupling of the radioisotope to protein, the vessel having means for the introduction and withdrawal of reagents when sealed;
    (b) introducing into the vessel the radioisotope and a buffer solution of the antibody to be labeled;
    (c) incubating the resulting reaction mixture under conditions which permit the labeling of the antibody;
    (d) introducing a resin which adsorbs the radioisotope which is not bound to antibody into the vial;
    (e) withdrawing the resin and the reaction mixture; and
    (f) separating the resin and the radiolabeled antibody.

2. A method of claim 1, wherein the antibody is a monoclonal antibody.

3. A method of claim 1, wherein the radioisotope is $^{123}I$, $^{125}I$, or $^{131}I$.

4. A method of claim 1, wherein the radioisotope is $^{111}In$ or $^{67}Ga$.

5. A method of claim 1, wherein the reaction vessel is sealed with a cap penetrable by a needle and reagents are introduced and withdrawn from the vessel by means of a syringe.

6. A method of claim 1, wherein the resin and the antibody are separated by sterile filtration.

7. A method of iodinating antibody comprising the steps of:

(a) placing an oxidizing reagent which catalyzes the coupling of iodine to antibody into a sealable reaction vessel, the vessel having means for introduction and withdrawal of reagents when sealed;
(b) sealing the vessel;
(c) introducing radioactive iodine and a buffer solution containing the antibody to be iodinated into the vessel to form a reaction mixture;
(d) incubating the resulting reaction mixture under conditions which permit iodination of the antibody;
(e) introducing into the vessel a resin which absorbs iodine to adsorb iodine which is not bound to the antibody;
(f) withdrawing the reaction mixture and the resin from the vessel; and
(g) separating the resin and the reaction mixture containing iodinated antibody.

8. A method of claim 7, wherein the antibody is a monoclonal antibody.

9. A method of claim 7, wherein the oxidizing reagent which catalyzes the coupling of iodine to antibody is 1,3,4,6-tetrachloro-3,6-diphenylglycuril, chloroamine T, lactoperoxidase or iodine monochloride.

10. A method of claim 7, wherein the radioactive iodine is $I^{125}$, $I^{131}$, or $I^{123}$.

11. A method of claim 7, wherein the buffer solution containing the antibody to be iodinated is a 0.1M borate buffer at about ph 8.0–8.5.

12. A method of claim 7, wherein the resin comprises a styrene divinyl benzene copolymer lattice having attached quarternary ammonium groups.

13. A method of claim 7, wherein the resin is added to the reaction vessel together with a carrier protein.

14. A method of claim 7, wherein the resin is separated from the iodinated antibody by filtration through a filter having a pore size less than the resin particle size.

15. A method of iodinating monoclonal antibody, comprising the steps of:

(a) providing a vial sealed under a vacuum by a cap penetrable by a needle, the inner surface of the vial being coated with 1,3,4,6-tetrachloro-3,6-diphenylglycuril;
(b) injecting into the vial a buffer solution of $I^{123}$, $I^{125}$, or $I^{131}$ in sodium hydroxide;
(c) injecting into the vial a buffer solution of monoclonal antibody to be iodinated in a borate buffer at ph 8.0–8.5;
(d) incubating the resulting reaction mixture under conditions which permit iodination of the antibody;
(e) injecting into the vial a mixture comprising a resin which absorbs iodine that is not coupled to the antibody and a carrier protein;
(f) withdrawing the reaction mixture and the resin from the vial into a syringe; and
(g) separating the resin from the reaction mixtrure containing iodinated antibody by injecting the mixture through a filter having a pore size of about 0.22 microns.

16. A method of claim 15, wherein the resin is an anion exchange resin comprising a styrene divinyl benzene copolymer lattice having attached quarternary ammonium groups.

17. A method of claim 15, wherein the carrier protein is bovine serum albumin.

18. A kit for radioiodinating protein, comprising;
a. a vacuum sealed reaction vial the inner surfaces of which is coated with 3,4,6-tetrachloro 3,6-diphenylglycuril, the vial having means for injection and withdrawal of reagents by syringe when the vial is sealed; and
b. a vial containing a suspension of a resin which adsorbs iodine in buffer solution.

19. A kit of claim 18, further comprising:
c. a filter having a pore size of about 0.22 microns.

20. A kit of claim 18, wherein the resin comprises a styrene divinyl benzene copolymer lattice having attached quarternary ammonium groups.

* * * * *